US 6,616,663 B2

(12) United States Patent
Glenn, III et al.

(10) Patent No.: US 6,616,663 B2
(45) Date of Patent: Sep. 9, 2003

(54) BONE-ANCHOR LOADING DEVICES AND METHODS OF USE THEREFOR (75) Inventors: Melvin L. Glenn, III, Spencer, IN (US); Gary D. Wood, Spencer, IN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/834,675

(22) Filed: Apr. 13, 2001

(65) Prior Publication Data
US 2002/0151891 A1 Oct. 17, 2002

(51) Int. Cl.$^7$ .................................................. A61F 5/04
(52) U.S. Cl. .......................................................... 606/53
(58) Field of Search ............................... 606/53–86, 99, 606/104; 81/13, 44

(56) References Cited

U.S. PATENT DOCUMENTS

| 4,140,161 A | * | 2/1979 | Russo et al. ................... 145/52 |
| 4,581,962 A | * | 4/1986 | Marbourg ..................... 81/451 |
| 4,738,255 A | | 4/1988 | Goble et al. .................. 128/92 |
| 4,968,315 A | | 11/1990 | Gatturna ..................... 606/72 |
| 5,002,550 A | | 3/1991 | Li .............................. 606/139 |
| 5,100,417 A | | 3/1992 | Cerier et al. ................. 606/139 |
| 5,102,421 A | | 4/1992 | Anspach, Jr. ................ 606/232 |
| 5,207,679 A | | 5/1993 | Li .............................. 606/72 |
| 5,534,012 A | | 7/1996 | Bonutti ....................... 606/232 |
| 5,649,931 A | * | 7/1997 | Bryant et al. ................ 606/104 |
| 5,667,513 A | * | 9/1997 | Torrie et al. ................. 606/104 |
| 5,860,983 A | | 1/1999 | Wenstrom, Jr. ............. 606/104 |
| 5,948,001 A | | 9/1999 | Larsen ....................... 606/232 |
| 5,972,000 A | | 10/1999 | Beyar et al. ................ 606/139 |
| 5,993,459 A | | 11/1999 | Larsen et al. ............... 606/104 |
| 6,189,422 B1 | * | 2/2001 | Stihl .......................... 81/452 |

FOREIGN PATENT DOCUMENTS

| EP | 0 611 551 | 2/1993 |
| FR | 2 771 621 | 6/1999 |
| WO | WO 96/32890 | 10/1996 |

OTHER PUBLICATIONS

In–Fast™, Bone Screw System.

* cited by examiner

Primary Examiner—Todd E. Manahan
(74) Attorney, Agent, or Firm—Testa, Hurwitz & Thibeault, LLP (57) ABSTRACT A device and method of loading a bone anchor into a bone-anchor inserter does not apply force on the leading point, the distal cutting edges or threads of the bone anchor. The bone-anchor loading device may, for example, include a main body including a gripping portion and, projecting therefrom, an elongated bone-anchor receiving member having a receiver fitting at a distal end thereof; an elongated sleeve coaxially disposed over the anchor-receiving member and configured for slidable translation thereover; and an interference fitting causing engagement between the sleeve and the anchor-receiving member when the sleeve is translated to an interference position with respect to the main body, the engagement further causing the receiver fitting to deform to releasably secure a bone anchor.

7 Claims, 8 Drawing Sheets

BONE-ANCHOR LOADING DEVICES AND METHODS OF USE THEREFOR

TECHNICAL FIELD

This invention relates to devices for loading bone anchors into bone-anchor insertion devices and methods of using such bone-anchor loading devices.

BACKGROUND INFORMATION

Bone anchors are used in surgical procedures to create attachment sites for surgical implants such as sutures, patches, or slings. Bone anchors may be divided into two general categories: bone anchors that require pre-drilling and self-tapping bone anchors. Self-tapping bone anchors are more efficient than those requiring pre-drilling because the use of self-tapping bone anchors collapses three steps (i.e., pre-drilling into bone, locating the pre-drilled hole, and inserting the bone anchor into the pre-drilled hole) into a single step.

Self-tapping bone anchors generally include a sharp leading tip, an inserting feature, a retaining feature, and a suture attachment site. Some bone anchors are configured as conical screws in which the inserting and retaining functions are served by threading which covers the entire shank beginning at a sharp distal tip. Other bone anchors are configured as drill bits in which the inserting function is served by a fluted cutting surface terminating in a sharp leading tip at the distal end of the shank; the retaining function is accomplished by threading located at the proximal end of the shank. Bone anchors configured as screws or drill bits may be introduced into bone using a rotary bone-anchor inserter, e.g., a drill.

Other self-tapping bone anchors are configured without any threading. In such bone anchors a sharp leading tip, such as a biomet crown, serves the insertion function and wings positioned on the shank serve the retaining function. Such bone anchors may be introduced into bone by applying linear force upon the bone anchor using a press-in type bone-anchor inserter device.

Many bone-anchor inserter devices are delivered to the surgeon in sterile packaging with the bone anchor preloaded and, optionally, the suture preattached. In surgical procedures requiring more than one bone anchor, the surgeon may reload the bone-anchor inserter device manually.

Manual loading of a bone anchor into a bone-anchor inserter may be accomplished by pinching the bone anchor between two fingers at the sharp distal end of the shank, aligning the shaft of the bone anchor with the mount of a bone-anchor inserter, and pushing the bone anchor into the bone anchor mount. This is an awkward and time-consuming procedure, which presents risks to both the patient and the surgeon. One potential risk is that the surgeon may drop the small bone anchor while attempting to manipulate it. A more serious risk is that the surgeon may puncture his or her surgical gloves and/or skin, and thus cause injury to the surgeon and breach the sterility of the bone anchor, the bone-anchor inserter, and/or the operating area.

One known bone-anchor loading device engages the bone anchor by the distal end of the shank, which can dull the bone anchor threads or the fluted cutting edges located on the distal end of the shank, making insertion of the bone anchor into the bone difficult. Likewise, this bone-anchor loading device deploys the bone anchor into the bone-anchor inserter by applying linear force upon the sharp distal tip of the bone anchor, which may damage the distal tip and thereby complicate insertion of the anchor into the bone. Furthermore, very little force is required to deploy a bone anchor from this bone-anchor loading device and, therefore, the bone anchor may deploy before the shaft of the bone anchor is properly seated in the mount of the inserter.

Accordingly, there is a need for a device and method of loading a bone anchor into a bone-anchor inserter that is safe and efficient. There is a further need for a device and method of loading a bone anchor into a bone-anchor inserter that does not apply damaging forces upon the leading point, the distal cutting edges and/or the distal threads of the bone anchor.

SUMMARY OF THE INVENTION

The present invention provides a bone-anchor loading device useful for efficiently and safely loading a bone anchor into a bone-anchor inserter without applying force on the leading tip, the distal cutting edges, and/or the distal threads of a bone anchor. The device is conveniently used, reliable, and can be dimensionally matched to standard bone-anchor inserters to facilitate interoperation therewith.

In some embodiments, the bone-anchor loading device comprises a main body including a gripping portion, a bone-anchor receiving member, and an elongated sleeve. The elongated sleeve may be coaxially disposed over the bone-anchor receiving member and configured for slidable translation thereover. The bone-anchor loading device may also include an interference fitting that engages when the sleeve is translated to an interference position with respect to the main body. The engagement between the sleeve and bone-anchor receiving member causes the receiver fitting to releasably secure a bone anchor.

Some embodiments of the invention may also include an alignment feature to maintain a fixed angular orientation between the receiving member and the sleeve. Accordingly, the bone-anchor loading device may further comprise an alignment recess formed in one of the sleeve and the anchor-receiving member, and an alignment-recess mate projecting from the other of the sleeve and the anchor-receiving member. The alignment recess mate may be configured to slidably couple with the recess and prevents rotation between the sleeve and the receiving member. The alignment recess may have an axial length along the longitudinal axis determining at least one stop position. The stop position may limit travel of the sleeve relative to the anchor-receiving member when the sleeve is extended relative to the anchor-receiving member and/or when the sleeve is retracted relative to the anchor-receiving member.

In some embodiments, the alignment recess may be one or more slots extending fully through one of the sleeve and the anchor-receiving member, and the alignment recess mate may be a guide pin secured to the other of the sleeve and the anchor-receiving member. In one preferred embodiment, the alignment recess mate is a guide pin secured to the elongate bone-anchor receiving member, the sleeve includes a pair of opposing slots, and the guide pin has a length greater than the diameter of the receiving member such that each of the opposing slots travels along the guide pin.

In some alternative embodiments, the elongated bone-anchor receiving member and the elongated sleeve have off-round profiles.

In some embodiments, the gripping portion may comprise a pair opposing flat surfaces that may, optionally, include raised ridges or other texturing to provide a firm gripping surface.

In one embodiment, the engagement between the sleeve and the anchor-receiving member applies tension on the receiver fitting, thereby causing the receiver fitting to engage a bone anchor loaded in the receiver fitting. In a preferred embodiment, the retention forces are applied only to the proximal end of the bone-anchor shank. For example, the receiver fitting may be a split conical recess located at the distal end of the receiver fitting and adapted to receive the distal portion of a conical bone anchor.

In preferred embodiments, the receiver fitting comprises deformable material and an interference fit results from inward radial force being applied upon the receiver fitting. The inward radial force may result from an enlarged outer diameter on the distal end of the receiver fitting contacting a narrowed inner diameter on the proximal end of the sleeve. In preferred embodiments, the anchor-receiving member and the sleeve cooperate to release the bone anchor without exerting force on the distal end of the bone anchor including, the sharp leading tip, and where applicable, the distal cutting surface and/or the distal threading of the bone anchor.

The bone-anchor loading device may, optionally, include at least one wing disposed on the outer surface of the sleeve, which is configured to facilitate positioning the sleeve and receiving member into the interference position when a bone anchor is positioned within the deformable receiver member. In some embodiments, the wing may be in the form of a collar disposed on the outer surface of the sleeve. In other embodiments, a pair of wings may be oppositely disposed on the outer surface of the sleeve.

In some embodiments, the distal end of the sleeve is transparent to permit visualization of at least the shaft of a bone anchor loaded in the bone-anchor loading device.

In some embodiments, the bone-anchor loading device is preloaded with a bone anchor, and optionally, a preattached suture.

In another aspect, the invention features methods of loading a bone anchor into a bone-anchor inserter. Embodiments of this aspect of the invention include the following features.

In one embodiment, the method of the invention comprises the steps of providing a bone-anchor loading device configured to releasably retain a bone anchor by the distal end of the bone-anchor shank; loading a bone anchor into the loading device; causing retention of the bone anchor therein; coupling the loading device with the inserter so as to seat the bone anchor within the inserter; and operating the loading device to release the seated bone anchor into the inserter.

The bone-anchor loading device may comprise a main body including a gripping portion and, projecting therefrom, an elongated bone-anchor receiving member having a receiver fitting at a distal end thereof; an elongated sleeve coaxially disposed over the anchor-receiving member and configured for slidable translation thereover; and an interference fitting causing engagement between the sleeve and the anchor-receiving member when the sleeve is translated to an interference position with respect to the main body, the engagement further causing the receiver fitting to deform to releasably secure a bone anchor.

In some embodiments, the operating step comprises pushing the body of the bone-anchor loading device toward the bone-anchor inserter. The operating step may further comprise forcing the distal end of the sleeve proximally toward the gripping portion of the main body to thereby relieve the interference fit and release the bone anchor from the bone-anchor loading device.

In preferred embodiments, force is not applied upon a leading tip of the bone anchor during the loading and the operating steps, nor is force applied upon a cutting surface or the distal threading of the bone anchor during the loading and the operating steps.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1:
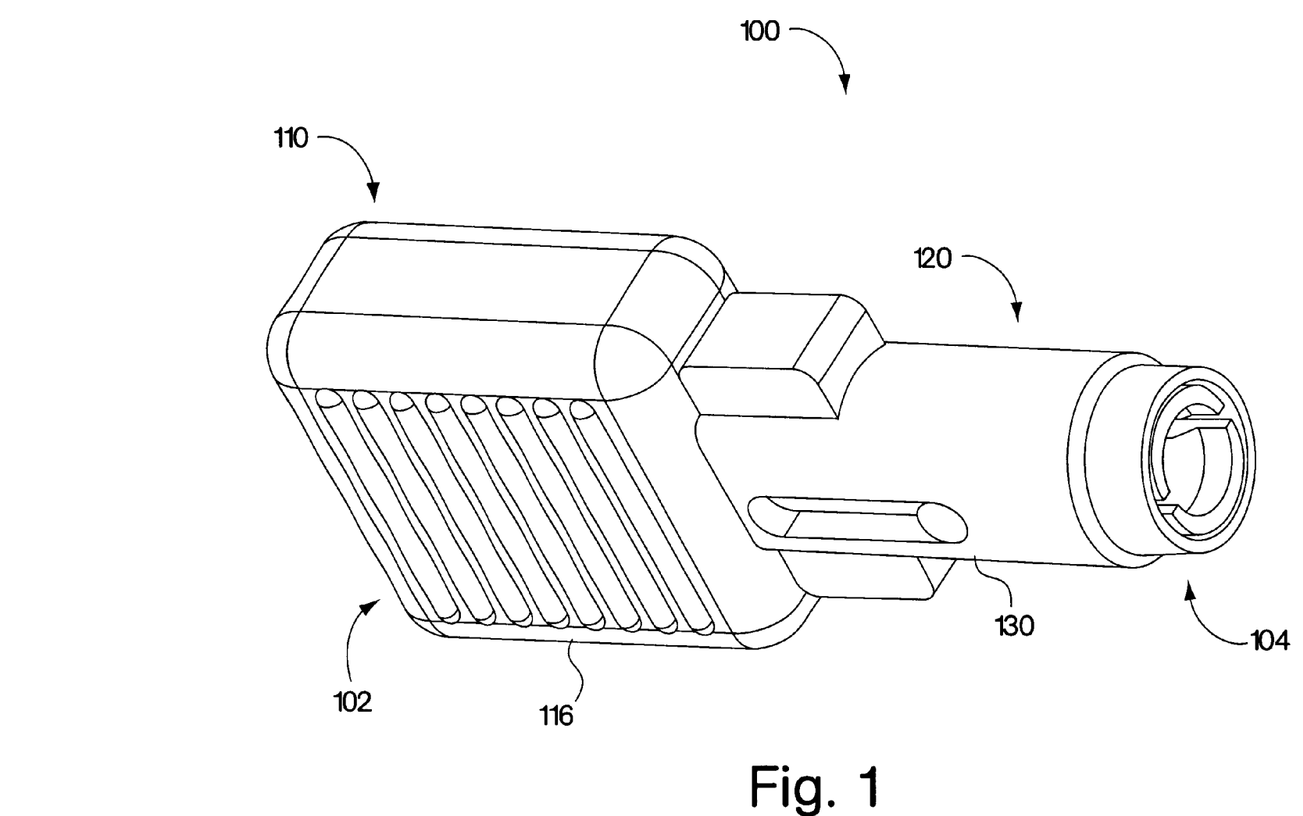
FIG. 1 is an isometric view of a bone-anchor loading device in accordance with the present invention.

With reference to FIG. 1, one embodiment of the bone-anchor loading device 100 of the invention comprises a main body 110 and an elongated sleeve 120. Generally, the bone-anchor loading device includes a proximal end 102 and a distal end 104. The main body itself 110 includes a proximal end 112, a distal end 114, a gripping portion 116 and, projecting therefrom, an elongate bone-anchor receiving member 130. The elongated sleeve 120 is coaxially disposed over the bone-anchor receiving member 130, and is configured for slidable translation thereover.

The gripping portion 116 of the device is sized and configured to be easily gripped by the operator. The gripping portion 116 of the device may have opposing flat surfaces as shown. As illustrated, the gripping portion 116 of the main body 110 is generally rectangular in shape with rounded edges. In some embodiments, the gripping portion 116 may include texturing to provide a firm gripping surface. As shown in FIG. 1, the texturing may be in the form of raised ridges.

The device of the present invention may generally be formed with rounded edges to reduce sharp surfaces that could potentially tear a surgical glove or cut the skin of the user. The device of the invention may be fabricated from a rigid material, e.g., a rigid plastic such as polycarbonate. In some embodiments, the bone-anchor loading device is pre-loaded with a bone anchor, and optionally, a suture.

The elongated sleeve 120, shown in detail in FIGS. 2B, 3B, 4A, 4B, and 6A–7C, is configured to be coaxially disposed over the bone-anchor receiving member 130. Thus, in preferred embodiments, the interior shape of the elongated sleeve 120 will substantially match the exterior shape of the bone-anchor receiving member 130. For example, in embodiments where the bone-anchor receiving member is cylindrical, the elongated sleeve is cylindrical as well. Likewise, in embodiments where the bone-anchor receiving member is elliptical, the elongated sleeve is elliptical, and in embodiments where the bone-anchor receiving member is off-round with one or more flat surfaces, the sleeve is also off-round with a matching number of flat surfaces. In alternative embodiments, the sleeve 120 and the bone-anchor receiving member 130 have complementary mating surfaces that are geometrically dissimilar. As shown in FIGS. 4A, 4B, and 6A–7C, the sleeve 120 generally includes a proximal inner diameter 132 and a distal inner diameter 133 configured to cooperate with the outer surfaces of the bone-anchor receiving member 130 to create an interference fit.

One embodiment of the elongated bone-anchor receiving member 130 is shown in FIGS. 2A, 3A, 5A, 5B, and 6A–7C. In this embodiment the receiving member 130 is a cylinder including a distal end 144 and a proximal end 145. A receiver fitting 146 is positioned at the distal end 144 of the bone-anchor receiving member 130. As described in greater detail below, when the sleeve is translated to an interference position with respect to the main body 110, the sleeve and the bone-anchor receiving member form an interference fitting. The receiver fitting 146 may include a conical recess 148, a split end 150, and a flared end 152. A conical recess may be formed during manufacture, for example, by creating a mold including a conical recess for injection molding.

The receiver fitting 146 generally includes a flared or enlarged outer diameter 152, as shown, and may also include an enlarged inner diameter (not shown). In preferred embodiments, outer dimensions of the bone-anchor receiving member 130 are configured to cooperate with the inner dimensions of the sleeve 120 to create an interference fit. In particular, the flared end 152 may have an enlarged outer diameter sized and configured to create an interference fit with the inner diameter of the sleeve 120. The interference fit results from inward radial force applied upon the receiver fitting 146 when the sleeve 120 is positioned in the interference position. The interference fit interoperates with the conical recess 148 to engage only the bone anchor as discussed below.

Figure 4A:
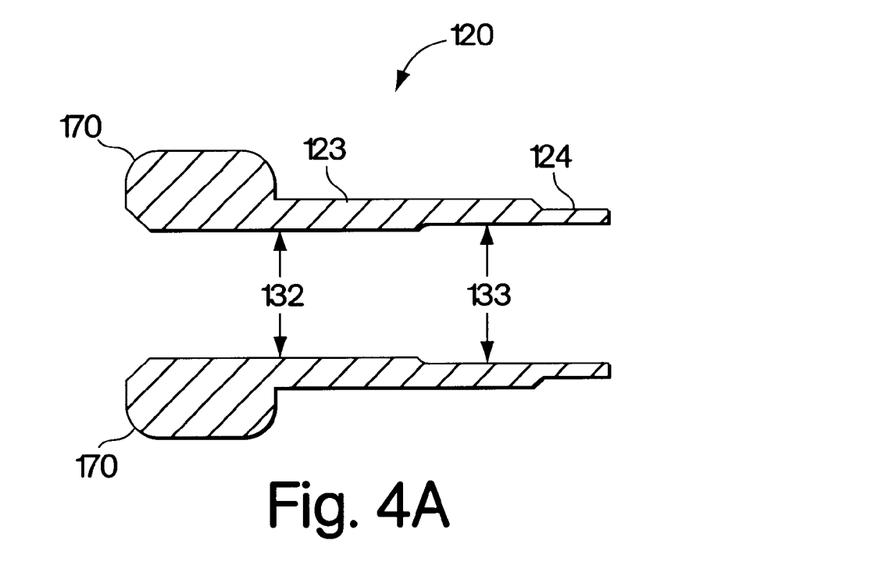
FIG. 4A is a cross-sectional view of the sleeve.
Figure 4B:
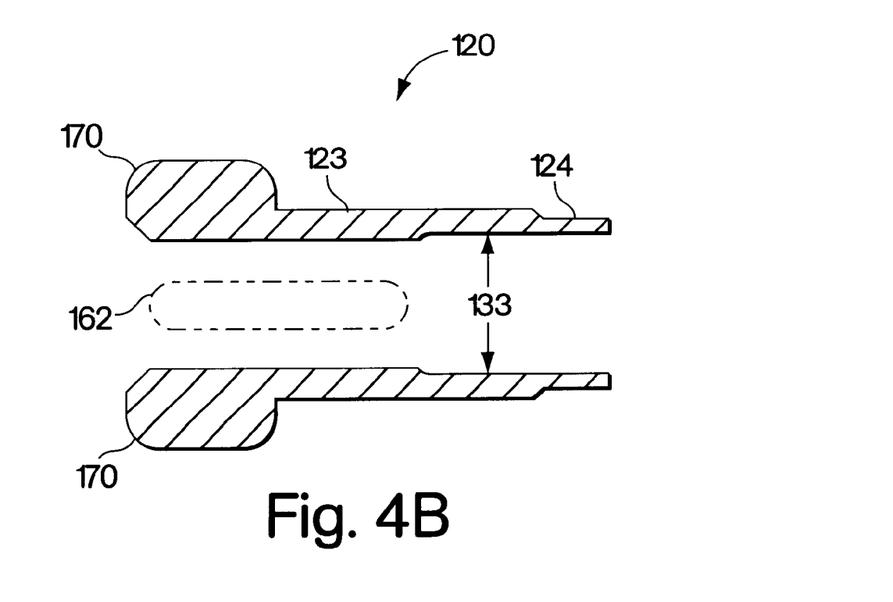
FIG. 4B is a cross-sectional view of the sleeve that depicts the alignment recess in shadow.
Figure 5A:
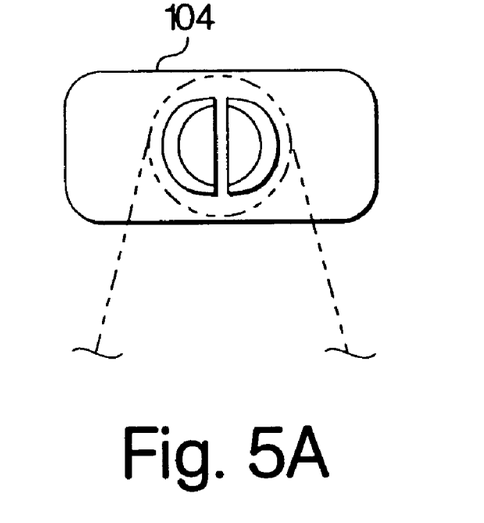
FIG. 5A is an end view of bone-anchor loading device.
Figure 5B:
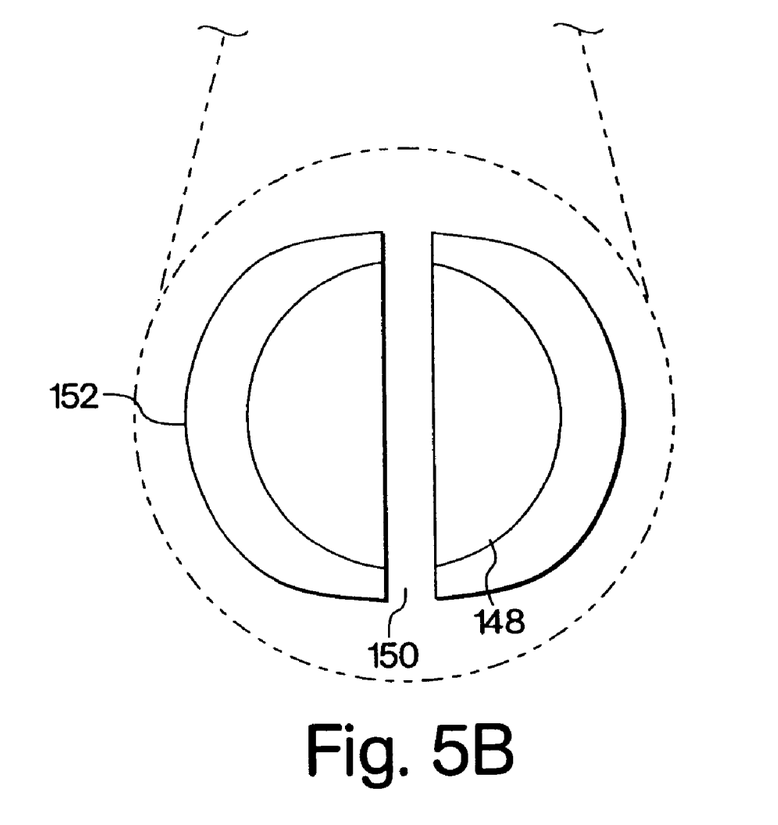
FIG. 5B is an enlarged end view of the bone-anchor loading device.

With reference to FIGS. 4A and 4B, in embodiments where the receiver fitting 146 is cylindrical, the sleeve 120 forms a generally cylindrical bore having a proximal inner diameter 132 and a larger distal inner diameter 133. In such embodiments, the outer surface of receiving member 130 and its flared end 152 are preferably sized for a loose sliding axial fit within proximal inner diameter 132 and distal inner diameter 133, respectively, of sleeve 120. When, however, the flared end 152 is engaged within the proximal inner sleeve diameter 132, the result is an interference fit. In one preferred embodiment (best shown in FIGS. 5A, 5B), the distal end of the cylinder is split to permit radial inward deformation of the receiver fitting 146. The split may be positioned in the center of the cylinder or may be offset. It should also be noted that sleeve 120 may have different outer diameters 123, 124 along its axial length to simplify manufacture.

Operation of the devices is illustrated in FIGS. 6A–7C. As shown therein, the sleeve 120 of the bone-anchor loading device 100 may be placed in three general positions, namely, the retracted loading/deployment position, the intermediate position, and the extended interference position.

Figure 6A:
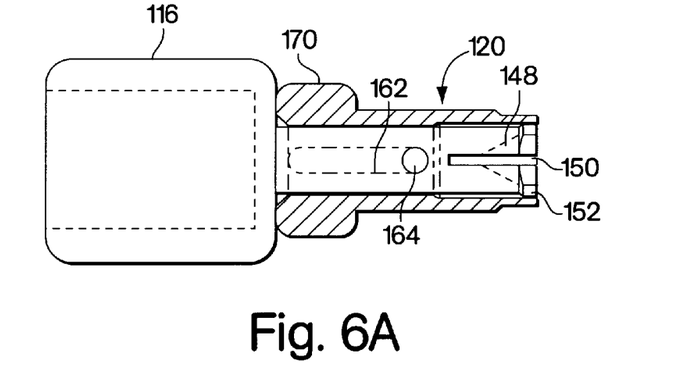
FIG. 6A is a plan view of the bone-anchor loading device when the sleeve is positioned in the retracted loading/deployment position.
Figure 7A:
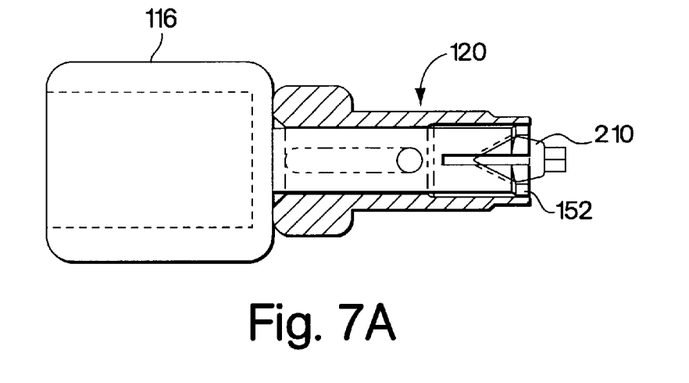
FIG. 7A is a plan view of bone-anchor loading device loaded with a bone anchor where the sleeve is positioned in the retracted loading/deployment position.

FIGS. 6A, 7A show the bone-anchor loading device 100 in the retracted loading/deployment position. In this position the flared end 152 of the bone-anchor receiving member 130 resides within the distal inner diameter of the sleeve 120 (which is larger than the proximal inner diameter). Thus, the receiver fitting 146 is in an open, unstressed position adapted to load or deploy a bone anchor 210. Accordingly, a preliminary step in inserting a bone anchor 210 into the bone-anchor loading device 100 of the invention is to position the bone-anchor loading device 100 into the retracted loading/deployment position.

Figure 6B:
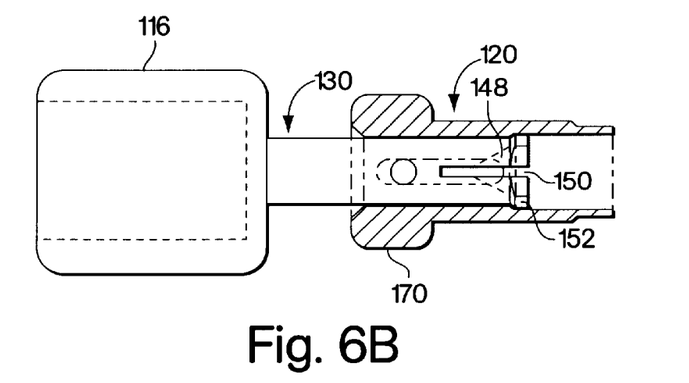
FIG. 6B is a plan view of the bone-anchor loading device when the sleeve is positioned in the intermediate or pre-interference position.
Figure 7B:
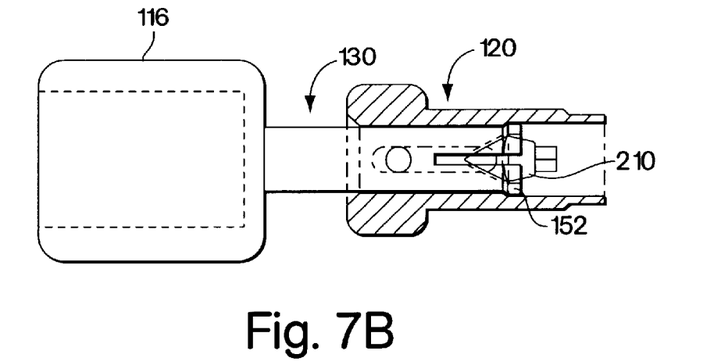
FIG. 7B is a plan view of bone-anchor loading device loaded with a bone anchor where the sleeve is positioned in the pre-interference position.

FIGS. 6B, 7B depict the bone-anchor loading device 100 in the intermediate position. In this position the flared end 152 of the bone-anchor receiving member 130 lies within the distal inner diameter of sleeve 120 and in contact with the shoulder defining the onset of the narrower proximal inner diameter. This represents the furthest extended position of sleeve 120 before the interference fit occurs. Accordingly, the machine or the surgeon will extend the sleeve 120 to the pre-interference position shown in FIGS. 6B, 7B just prior to forcing the sleeve 120 into the interference position in order to capture the bone anchor.

Figure 6C:
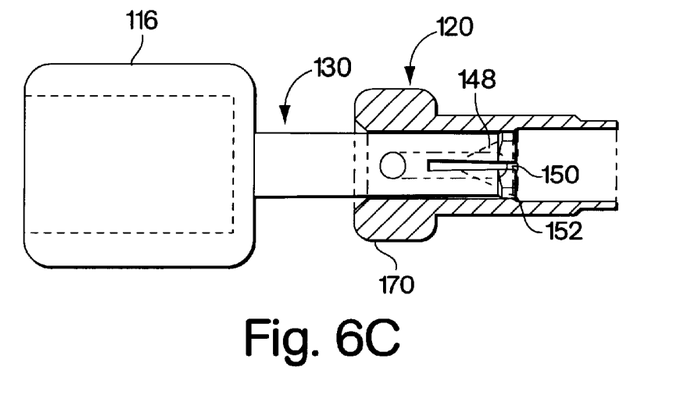
FIG. 6C a is plan view of the bone-anchor loading device when the sleeve is positioned in the extended interference position
Figure 7C:
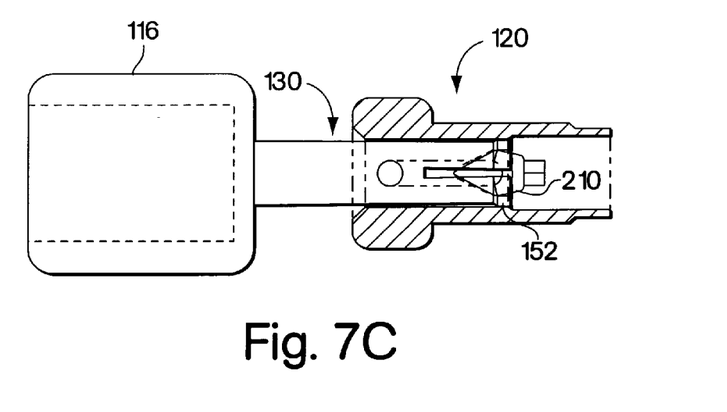
FIG. 7C is a plan view of bone-anchor loading device loaded with a bone anchor where the sleeve is positioned in the extended interference position.

As shown in FIGS. 6C, 7C, the receiver fitting 146 is compressed inwardly when the flared end 152 of receiving member 130 enters the proximal inner diameter of sleeve 120, thereby gripping the bone anchor that the surgeon has previously loaded. The receiver fitting 146 is configured to deform only the distal end of receiver member 130, thereby minimizing the forces experienced by the sharp leading tip, the fluted cutting edges, and/or the threads of a bone anchor 210, since these are not engaged within (i.e., they have proximally cleared) the compression region.

The distal end of the sleeve 120 extends beyond the distal end of the anchor-receiving member when the sleeve 120 is positioned in the extended interference position shown in FIGS. 6C and 7C. In such embodiments at least the distal end of the sleeve 120 is preferably transparent for convenient visualization of the shaft of a bone anchor loaded in the bone-anchor loading device 100 and to thereby facilitate alignment of the shaft of the bone anchor 210 with a mount of a bone-anchor inserter device.

Figure 8:
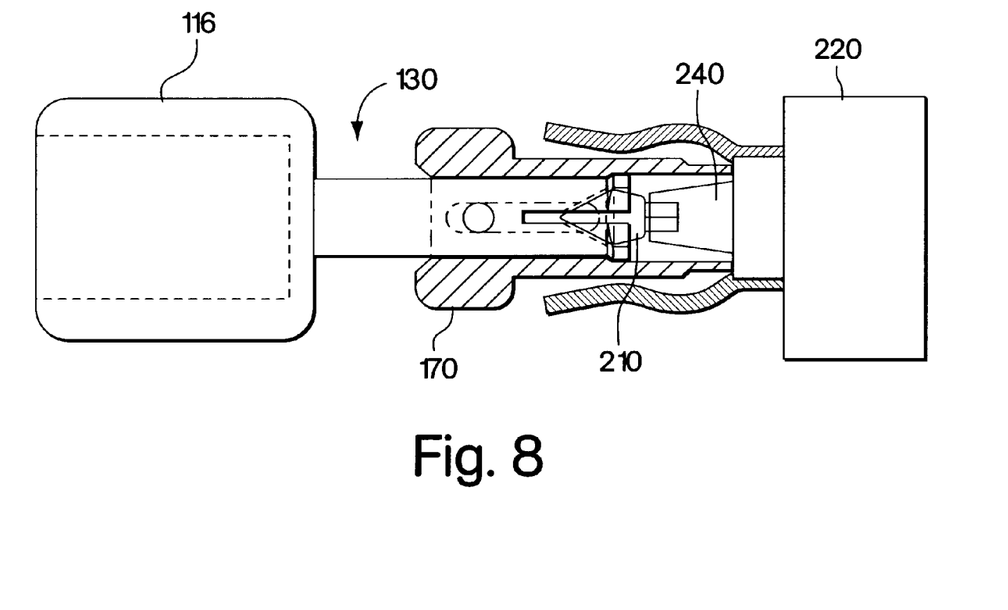
FIG. 8 is a plan view of the bone-anchor loading device loading a bone anchor into the mount of a bone-anchor inserter.

The bone-anchor loading device 100 may, for example, be deployed by pressing the bone-anchor loading device 100 into the mount 240 (see FIG. 8) of a bone-anchor inserter device 220, causing sleeve 120 to retract, the interference fitting to release, and the receiver fitting 146 to return to the unstressed, open position, thereby releasing the bone anchor. In preferred embodiments, the length of the distal end of the sleeve 120 is sized to correspond with a bone anchor mount 240 such that the sleeve 120 would not be retracted beyond the interference position until after the shaft of the bone anchor is seated within the bone anchor mount 240, thereby ensuring that the bone anchor is not prematurely deployed.

Figure 2A:
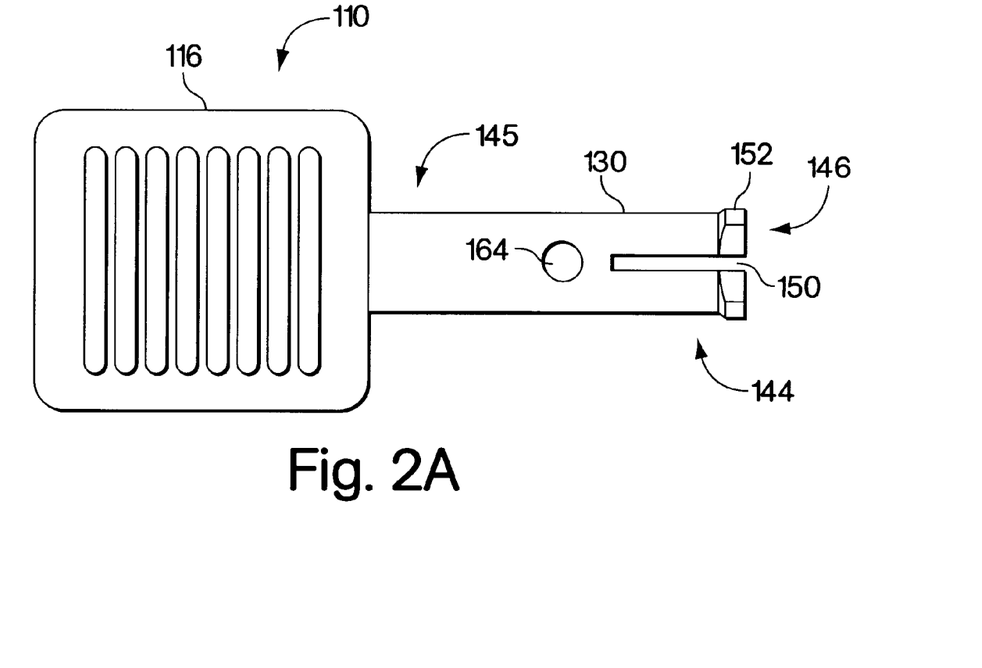
FIG. 2A is a plan view of the main body.
Figure 2B:
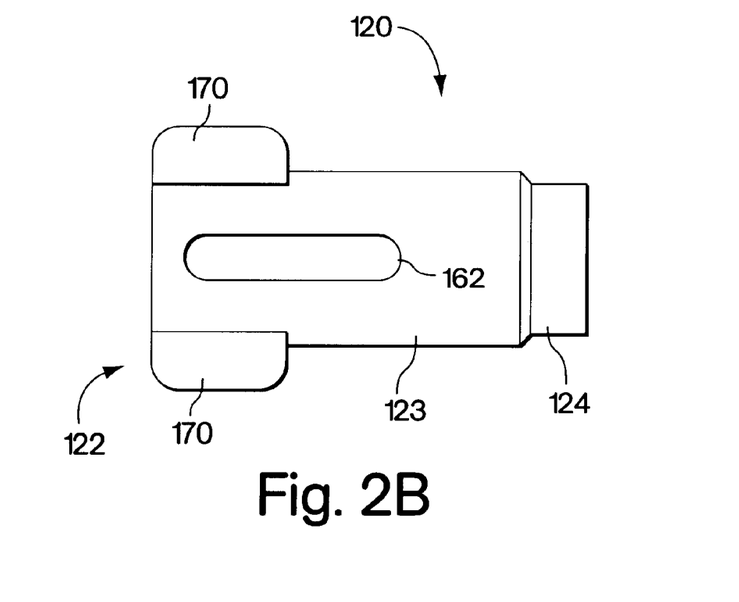
FIG. 2B is a plan view of the sleeve.
Figure 3A:
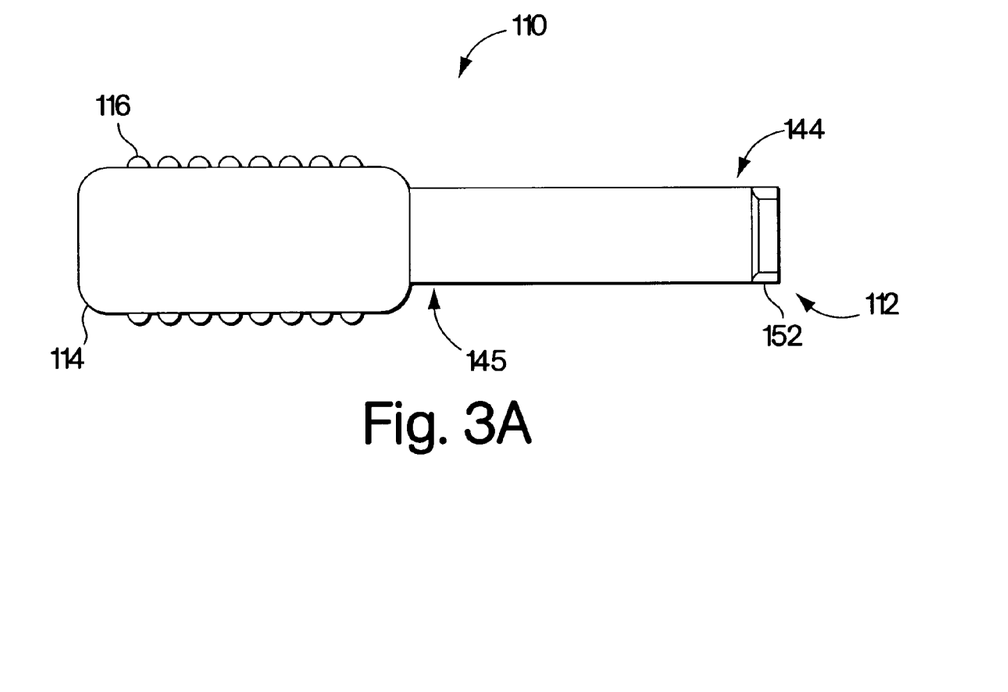
FIG. 3A is a side view of the main body.
Figure 3B:
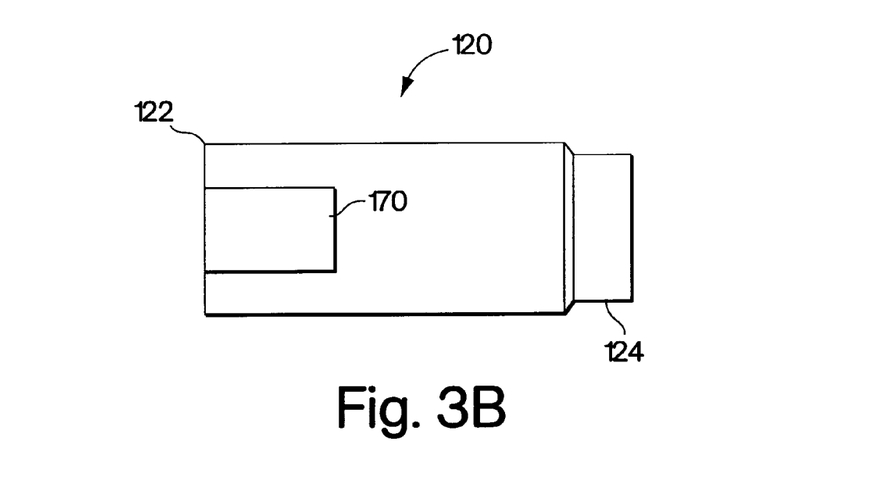
FIG. 3B is a side view of the sleeve.

Some embodiments of the invention may also include an alignment feature to maintain a fixed angular orientation between the receiving member 130 and the sleeve 120. In the absence of an alignment feature, the sleeve 120 would be free to rotate with respect to the receiving member 130. Such rotation may interfere with operation of the device. With reference to FIGS. 2A, 2B and 6A, the alignment feature may include an alignment recess 162 formed in one of the elongated sleeve 120 and the bone-anchor receiving member 130 and an alignment-recess mate 164 projecting from the other of the sleeve 120 and the bone-anchor receiving member 130. Alignment-recess mate 164 is slidably received within alignment recess 162 to permit translation but prevent rotation of the sleeve 120. In these embodiments, the alignment recess 162 may have an axial length along the longitudinal axis of the device 100 determining at least one stop position. A stop position is defined by an axial end of the alignment recess 162 which, when reached by alignment-recess mate 164, prevents further translation of sleeve 120 relative to anchor-receiving member 130. For example, the axial length of the alignment recess 162 may define a stop position when the sleeve 120 is in the retracted position (FIGS. 6A, 7A) and/or when the sleeve 120 is in the extended interference position (FIGS. 6C, 7C).

In the illustrated embodiments, the alignment recess 162 is a slot and the alignment-recess mate 164 is a projection, such as a guide pin. In the embodiment shown in FIG. 1 the slot 162 is located on the sleeve 120 and the guide pin 164 projects from the bone-anchor receiving member 130. Alternatively, the alignment recess 162 may be located on the bone-anchor receiving member 130 and the alignment-recess mate 164 may be located on the sleeve 120. It should be noted that the alignment recess may be a slot extending fully through the thickness of sleeve 120 or receiving member 130, as shown, or may instead be a recess extending only partially through that thickness. It should further be noted that the device 100 may include a pair of opposing pins and slots disposed on opposite sides of the sleeve 120 and the receiving member 130. For example, the guide pin may extend through and project beyond the receiving member 130 (i.e., may have a length greater than a diameter of the receiving member) such that each of two opposing slots on sleeve 120 travels along the guide pin.

In alternative embodiments the alignment feature is formed by configuring the bone-anchor receiving member and the elongated sleeve 120 with off-round profiles. For example, the bone-anchor receiving member 130 and the elongated sleeve 120 may have matching elliptical shapes that restrict rotational movement of the bone-anchor receiving member and the elongated sleeve 120. Likewise, the bone-anchor receiving member 130 and the sleeve 120 may have matching profiles including one or more flat segments such as a hexagonal shape, a semi-circle, or any other off-round shape defined by one or more flat surface(s).

In some embodiments, the sleeve 120 may include at least one wing 170. The wing 170 may be a collar or other protrusion extending from the sleeve 120 to provide a contact surface for forcing the sleeve 120 into the extended interference position with relation to the main body 110. The sleeve 120 shown in FIG. 2A includes a pair of wings. The wings 170 are preferably positioned on the proximal end 122 of the sleeve 120. However, the wings 170 may optionally be located at the central portion 123 or the distal end 124 of the sleeve 120 to provide a contact surface to force the sleeve 120 into the extended interference position. In general, the wings 170 are placed so as not to interfere with the alignment feature. Therefore, in embodiments where the alignment feature includes a slot in the central 123 portion of the sleeve 120, the wings are preferably placed at the proximal end 122 or the distal end 124 of the sleeve 120.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method of loading a bone anchor into a bone-anchor inserter, the bone anchor having a shank with a distal end, the method comprising the steps of:

providing a bone-anchor loading device configured to releasably retain a bone anchor by the distal end of the shank;

loading a bone anchor into the loading device and causing retention of the bone anchor therein;

coupling the loading device with the inserter so as to seat the bone anchor within the inserter; and operating the loading device to release the seated bone anchor into the inserter.

2. The method of claim 1 wherein the bone-anchor loading device comprises:

a main body including a gripping portion and, projecting therefrom, an elongated bone-anchor receiving member having a receiver fitting at a distal end thereof an elongated sleeve coaxially disposed over the anchor-receiving member and configured for slidable translation thereover; and an interference fitting causing engagement between the sleeve and the anchor-receiving member when the sleeve is translated to an interference position with respect to the main body, the engagement further causing the receiver fitting to d1form to releasably secure a bone anchor.

3. The method of claim 2 wherein the operating step further comprises forcing the distal end of the sleeve proximally toward the gripping portion of the main body to thereby relieve the interference fit and release the bone anchor from the bone-anchor loading device.

4. The method of claim 1 wherein the operating step comprises pushing the body of the bone-anchor loading device toward the bone-anchor inserter.

5. The method of claim 1 wherein force is not applied upon a leading tip of the bone anchor during the loading and the operating steps.

6. The method of claim 1 wherein force is not applied upon a cutting surface of the bone anchor during the loading and the operating steps.

7. The method of claim 1 wherein force is not applied upon a distal threading of the bone anchor during the loading and the operating steps.

* * * * *